(12) United States Patent
Lanzi et al.

(10) Patent No.: US 9,186,462 B2
(45) Date of Patent: Nov. 17, 2015

(54) SYRINGE AND SAFETY DEVICE ASSEMBLY

(71) Applicants: Sylvain Lanzi, Chirens (FR); Pascal Dugand, Estrablin (FR); Thierry Rimlinger, L'Isle d'Abeau (FR)

(72) Inventors: Sylvain Lanzi, Chirens (FR); Pascal Dugand, Estrablin (FR); Thierry Rimlinger, L'Isle d'Abeau (FR)

(73) Assignee: NEMERA LA VERPILLIERE S.A.S. (FR)

( * ) Notice: Subject to any disclaimer, the term of this patent is extended or adjusted under 35 U.S.C. 154(b) by 234 days.

(21) Appl. No.: 13/717,302

(22) Filed: Dec. 17, 2012

(65) Prior Publication Data

US 2013/0184655 A1    Jul. 18, 2013

Related U.S. Application Data

(63) Continuation of application No. PCT/FR2011/051317, filed on Jun. 9, 2011.

(30) Foreign Application Priority Data

Jun. 17, 2010    (FR) .................................... 10 54815

(51) Int. Cl.
*A61M 5/00*    (2006.01)
*A61M 5/31*    (2006.01)
(Continued)

(52) U.S. Cl.
CPC ........... *A61M 5/3134* (2013.01); *A61M 5/3135* (2013.01); *A61M 5/326* (2013.01);
(Continued)

(58) Field of Classification Search
CPC . A61M 5/3135; A61M 5/3257; A61M 5/326; A61M 5/3273; A61M 5/3275; A61M 5/3271; A61M 5/3243; A61M 5/3245; A61M 5/3246; A61M 5/3254; A61M 5/3256; A61M 2005/3246; A61M 2005/3254; A61M 2005/32565; A61M 2005/2418; A61M 2005/3142
USPC .................. 604/187, 227, 232, 198, 197, 110
See application file for complete search history.

(56) References Cited

U.S. PATENT DOCUMENTS 4,122,836 A * 10/1978 Burnett .............................. 600/5
4,642,103 A *  2/1987 Gettig ........................... 604/234
(Continued)

FOREIGN PATENT DOCUMENTS

EP         2047879 A1    4/2009
FR         2830765 A1    4/2003
(Continued)

OTHER PUBLICATIONS

International Search Report Application No. PCT/FR2011/051317 Completed: Oct. 10, 2011; Mailing Date: Oct. 18, 2011 3 pages.

*Primary Examiner* — Matthew F Desanto
(74) *Attorney, Agent, or Firm* — St. Onge Steward Johnston & Reens LLC

(57) ABSTRACT

A syringe assembly including a syringe and a safety device, the syringe including a barrel of tubular shape, the safety device including a member of tubular shape referred to as a syringe support in which the barrel is arranged such that the syringe support and the barrel are secured on the same axis. The syringe barrel has a flange at a proximal end that is prevented from moving in translation between a peripheral bearing seat and an abutment of the support. Interposed between the seat and the flange, the assembly includes at least one compression pad between the seat and the flange and made of a material presenting a coefficient of friction relative to at least one of the materials of the flange and of the seat that is greater than the coefficient of friction of the materials of the flange and of the seat relative to each other.

11 Claims, 3 Drawing Sheets

(51) Int. Cl.
*A61M 5/32* (2006.01)
*A61M 5/24* (2006.01)

(52) U.S. Cl.
CPC ................ *A61M2005/2418* (2013.01); *A61M 2005/3104* (2013.01); *A61M 2005/3142* (2013.01); *A61M 2005/3264* (2013.01)

(56) References Cited

U.S. PATENT DOCUMENTS 5,382,235 A * 1/1995 Sak ............................... 604/110
7,601,140 B2 * 10/2009 Rossback et al. ............. 604/227
7,875,005 B2 * 1/2011 Nemoto ........................ 604/187
8,900,197 B2 * 12/2014 Crow ............................ 604/197
2006/0036216 A1 * 2/2006 Rimlinger et al. ............ 604/198
2007/0239117 A1 10/2007 Chelak et al.
2008/0154200 A1 * 6/2008 Lesch ........................... 604/135

FOREIGN PATENT DOCUMENTS

FR 2922455 A1 4/2009
WO 0141841 A2 6/2001

* cited by examiner

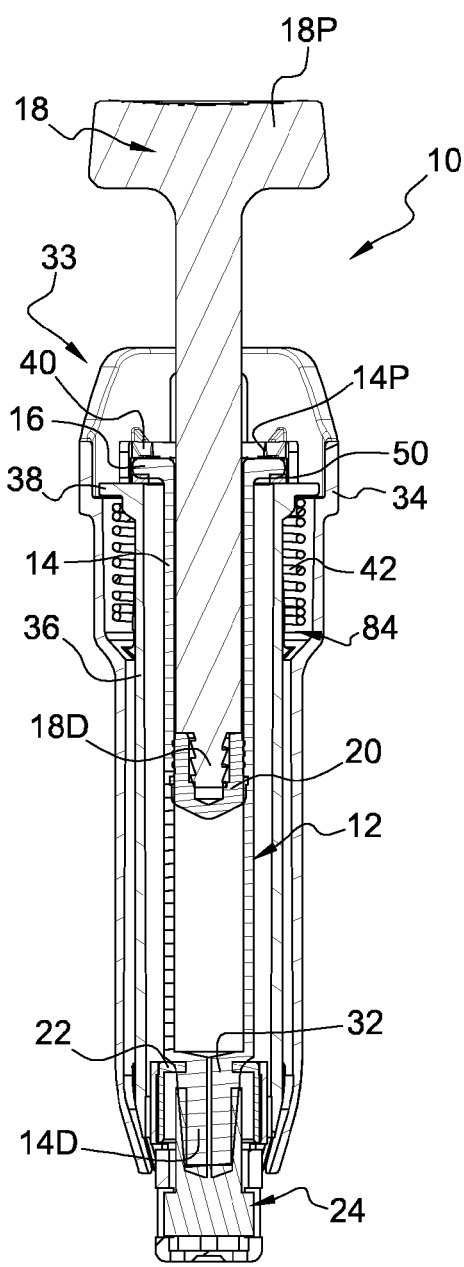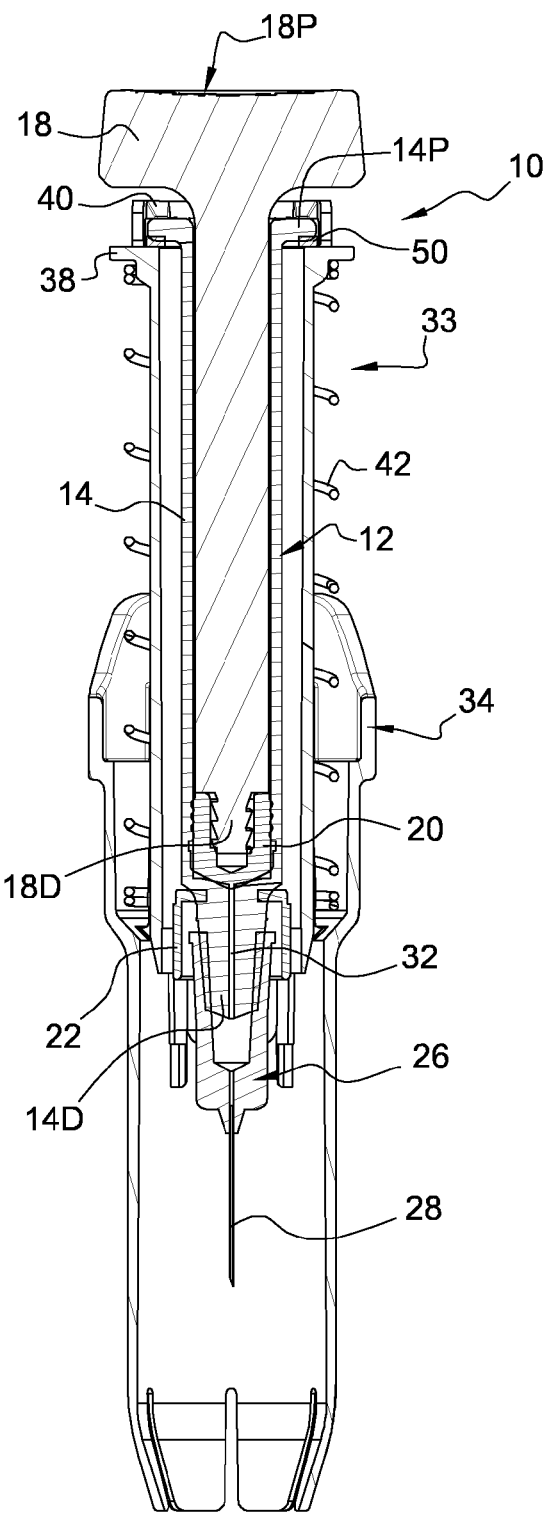
Fig. 1
Fig. 2

SYRINGE AND SAFETY DEVICE ASSEMBLY

FIELD OF THE INVENTION

The present invention relates to the field of safety devices for liquid-injection syringes, and in particular for prefilled syringes.

BACKGROUND OF THE INVENTION

In the prior art, and in particular from EP 2 047 879, a liquid-injection syringe is known of the type comprising a barrel of generally tubular shape forming a reservoir for the liquid and having fitted thereon an endpiece of generally annular shape for fastening a needle carrier on the syringe barrel.

The fastener endpiece is sometimes referred to as a "luer lock" and the needle carrier is sometimes referred to as a "luer hub".

The syringe also has a plunger mounted to move axially in the barrel between a ready position and a position at the end of injecting liquid.

Below, an element is referred to as being "proximal" or "distal" depending on whether it is axially close to or far from the end of the plunger that is to be actuated by a user.

EP 2 047 879 also describes a safety device for such a syringe, the safety device comprising:

a first member of generally tubular shape, referred to as a "protective sheath"; and a second member of generally tubular shape, referred to as a "syringe support", that is received in the sheath, substantially coaxially therewith.

The protective sheath and the syringe support are movable axially relative to each other between two positions that are referred to below as the "disengagement position" and as the "retraction position" of the syringe needle. The syringe barrel is secured axially to the syringe support. For this purpose, a flange situated at the proximal end of the syringe barrel is prevented from moving axially in a housing situated between a bearing seat and retractable abutments of the support, the flange having a small amount of slack due to the dispersion in the dimensions of the syringe barrel.

The safety device enables the needle to be retracted automatically into the sheath so as to avoid a person being accidentally pricked with the needle when handling the syringe assembly after it has been used normally, i.e. after injecting the liquid into the body of a patient.

The fastener endpiece has a proximal end that is generally engaged on a distal end of the syringe barrel that is generally conical in shape.

Furthermore, the fastener endpiece has a distal end for co-operating by screw-fastening with a needle carrier. This needle carrier and the needle it carries are covered by a cap prior to utilization of the syringe. Where applicable, prior to putting the needle carrier into place on the syringe barrel, a plug for closing the syringe barrel is screwed onto the fastener endpiece.

The torque needed for unscrewing the plug or for screwing on the needle carrier can lead to the syringe barrel turning relative to the safety device. It is therefore appropriate to be able to prevent the fastener endpiece from turning, in particular so as to be able to unscrew the plug or to screw on the needle carrier.

Unfortunately, once the syringe has been mounted in the safety device, the fastener endpiece is generally made practically inaccessible by the protective sheath that covers it. The user therefore cannot act directly on the fastener endpiece in order to prevent it from turning, in particular while unscrewing the plug or while screwing on the needle carrier.

For that purpose, the device described in EP 2 047 879 has a syringe support provided with first means for securing it in turning about its axis and comprising at least one pawl urged resiliently into a position in which the pawl co-operates with complementary means carried by the fastener endpiece for securing them in turning.

That enables the endpiece and the syringe support to be prevented from turning relative to each other and thus facilitates the operations of unscrewing the plug and of screwing on the needle carrier.

Nevertheless, the means for securing the syringe support with the endpiece can be activated only when the endpiece placed on the syringe barrel presents a particular shape, and in particular a ribbed shape. It is therefore not possible to use such a device for preventing a syringe from turning if it does not present that specific endpiece.

SUMMARY OF THE INVENTION

An object of the invention is to remedy that drawback by proposing a solution to the problem of preventing the syringe from turning in order to be able to unscrew the plug and screw on the needle carrier, which solution can be adapted to all types of syringe, regardless of the endpiece it carries.

To this end, the invention relates to a syringe assembly comprising a liquid-injection syringe and a safety device, the syringe comprising a barrel of generally tubular shape forming a reservoir for the liquid and the safety device comprising a syringe-support member in which the syringe barrel is arranged in such a manner that the syringe support and the syringe barrel are secured together axially, the syringe barrel having a flange at a proximal end that is prevented from moving in translation between firstly a peripheral bearing seat and secondly at least one abutment of the syringe support. The assembly also comprises at least one pad interposed between the seat of the support and the flange of the barrel, the pad being in compression between the seat and the flange, and being made of an elastic material.

The pad constitutes means for preventing the endpiece from turning relative to the syringe support. The pad may be fastened to the barrel or to the support, e.g. by adhesive, or it may be mounted between the barrel and the support. When it is mounted between the barrel and the support, the pad may be premounted between the seat and the abutment of the support or it may be engaged on the syringe barrel before they are assembled together.

When the syringe and the safety device are assembled together, the pad, which is compressed between the flange of the syringe barrel and the seat of the syringe support, acts, because of its contact with the flange and the seat, to exert an opposing torque that prevents the barrel from turning relative to the support even when sufficient torque is applied to the endpiece to enable the plug to be unscrewed or the needle carrier to be screwed on. This torque generated on the endpiece is transmitted between the endpiece and the barrel in particular as a result of the friction that exists between these two elements. It is then easy for the user to unscrew the plug and to screw on the needle carrier.

Such a pad eliminates the slack that exists in the prior art between the seat and the collar, and as a result it prevents the syringe barrel from turning relative to the syringe support. The fact that it is made of an elastic material makes it easier to assemble the assembly, and in particular makes it easier to mount the flange between the seat and the abutment, in spite of the dispersion in flange dimensions. Thus, the barrel is prevented from turning relative to the support in a manner that is passive, i.e. without any specific action or gesture being required on the part of the user in order to prevent the syringe from turning.

The pad presents a coefficient of friction with at least one of the materials of the flange or of the seat that is greater than the coefficient of friction relative to at least one of the materials of the flange and the seat relative to each other. This ensures that the opposing torque generated by the pad(s) is large and prevents any turning of the syringe barrel in the support, even when the user exerts a large force on the endpiece.

It should be observed that the support may be prevented from turning relative to the sheath by any means, and in particular by the means disclosed in EP 2 047 879, in order to further facilitate these operations.

In addition, since the pad is independent of the endpiece, it is possible to prevent any type of syringe from turning while unscrewing the plug, regardless of the endpiece that it carries.

The assembly of the invention is also less expensive than a prior art assembly, since the prior art requires the endpiece to be given a complex shape. The only element that is added, i.e. the pad, does not require any complex shape and it presents dimensions that are small. As a result it can be fabricated inexpensively.

The present invention may also comprise one or more of the characteristics in the following list:

The pad is formed by an annular ring. This embodiment is advantageous since this simplifies fabrication and assembly of the assembly, and therefore reduces manufacturing costs. The shape of the pad enables it to be engaged on the syringe barrel or to be placed on the device between the seat and the abutment while waiting for the barrel to be put into place in the support, thereby guaranteeing that the assembly can be assembled easily while avoiding any step of fastening the pad to the barrel or to the support.

At least one of the elements from the pad and the seat of the support present at least one projection. This also serves to facilitate assembling the assembly and to avoid damaging it. As defined above, the syringe flange is prevented from moving axially in the support between the seat and at least one abutment, generally a plurality of abutments. The distance between the seat and the abutments is defined. Nevertheless, it is known that manufacturing tolerances concerning the syringe barrel are rather slack and that as a result the thickness of the flange may vary in non-negligible manner. Since it is desired to place the pad in compression between the support and the barrel for all flange thicknesses, there can be no question of increasing the distance between the seat and the abutment. With thicker flanges, the abutment is thus liable to be subjected to a high level of stress once the flange has been inserted in the space between the abutment and the seat, in reaction to the pad being compressed by the flange, and this can lead to it being damaged or even broken.

Thus, the embodiment in which the pad and/or the seat has projections is very advantageous since the thickness of the pad can be reduced while nevertheless remaining in compression via the projections for all flanges. The compression force exerted on the pad and the reaction force exerted by the abutments is then smaller and there is no likelihood of the abutments being damaged, even with the thickest of flanges. All flanges, even the thinnest of flanges, are nevertheless suitable for compressing the pad so as to prevent the barrel from turning.

It is nevertheless possible to envisage an assembly in which both the seat and the pad are plane.

In a particular embodiment, the pad presents at least one projection, preferably a plurality of projections regularly distributed on a face in contact with the flange or with the seat. This embodiment is particularly simple to make and is therefore advantageous.

The projection is formed on the seat and is situated in a zone distinct from a zone facing the abutment. By way of example, the zone of the projection is interposed between two zones facing two abutments. This minimizes the stresses to which the abutments are subjected as a result of the presence of the pad, since the pad is compressed little in register with an abutment, while nevertheless preventing the syringe barrel from turning, in particular as a result of the pad being more compressed in zones in register with the projections, with this applying regardless of the thickness of the flange of the syringe.

Each of the projections of the seat and/or the pad is constituted by an element from the following list: a lug; a rib extending over at least a portion of the periphery of the pad or of the seat; and a radial rib.

The syringe barrel is made of glass or of plastics material and the syringe support is made of plastics material. The plastics material of the barrel and/or of the support being in particular based on polyethylene (PE), polypropylene (PP), polycarbonate (PC), polystyrene (PS), polyester (PET, PEN), styrenic polymers (SAN), acrylic polymers (PMMA), copolymers (MBS, SMMA terpolymers), polyvinyl chloride (PVC), copolyester (PETG, PCTG, PCTA), acrylonitrile-butadiene-styrene (ABS), cyclic polyolefins such as cyclo olefin polymer (COP) and cyclic olefin copolymers (COC), polyamide (PA), SB copolymer, styrene-ethylene-butylene-styrene (SEBS), polyether block amide (PEBA), poly(lactic-co-glycolic acid) (PLGA), polyactic acid (PLA), polyhydroxyalcanoates (PHA), polyhydroxybutyrate (PHB), cellulose propionate, cellulose acetate, and any mixture of these polymers and/or copolymers.

The pad is made of a thermoplastic or thermosetting elastomer material such as liquid silicone rubber (LSR), halogenated butyl rubber, non halogenated butyl rubber, nitrile rubber, thermoplastic ethylene-propylene-diene monomer (EPDM), a mixture of polypropylene and of cross-linked ethylene-propylene-diene monomer (PP/EPDM), thermoplastic polyurethane (TPU), and cross-linked polyurethane (PU), styrene thermoplastics, any mixture of these polymers and/or copolymers.

The protective sheath and the syringe support comprise complementary means for preventing them turning relative to each other about their axes, these means for preventing turning being activated at least when the sheath and the support are in their needle-disengaged relative position. These means comprise at least one complementary pair constituted by a projection and a groove arranged on the syringe support and on the protective sheath, and in particular two diametrically opposite pairs. The projection of the second means for preventing turning is arranged in particular on a proximal end of the syringe support and the groove of the second means for preventing turning is formed by a slot arranged in a proximal end of the protective sheath. These means make it even easier to unscrew the plug and to screw on the needle carrier.

The invention also provides a safety device for a liquid-injection syringe comprising a barrel of generally tubular shape forming a reservoir for the liquid, the safety device comprising a syringe support member in which the syringe barrel is arranged so that the syringe support and the syringe barrel are secured together axially, a flange of the syringe barrel situated at a proximal end of the barrel being prevented from moving in translation between firstly a peripheral bearing seat and secondly at least one support abutment of the syringe, wherein the device includes a pad mounted between the seat and the abutment and made of an elastic material, in particular an elastomer material.

The coefficients of friction of this material respectively relative to the material of the barrel (glass) and to the material of the support (plastics materials, as defined above) is in particular greater than the coefficient of friction between the materials of the support and of the barrel.

BRIEF DESCRIPTION OF THE DRAWINGS

The invention can be better understood on reading the following description made with reference to the figures, in which:

FIG. 1 is a section view of an assembly comprising a syringe and a syringe safety device, prior to injection;

FIG. 2 is a section view of the FIG. 1 assembly after injection;

DETAILED DESCRIPTION OF THE INVENTION

Figure 3:
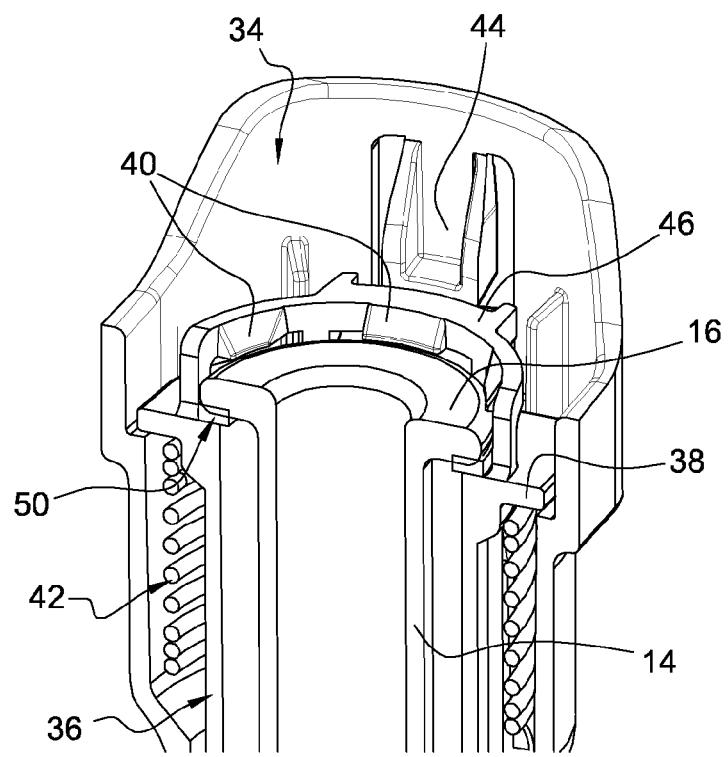
FIG. 3 is a perspective view of the proximal end of one-half of the assembly of FIGS. 1 and 2 from which the plunger has been removed.

FIGS. 1 to 3 show a syringe assembly of the invention given overall reference 10.

The assembly 10 comprises a conventional syringe 12 for injecting a liquid, in particular a medical liquid.

The syringe 12 comprises a tubular syringe barrel 14 forming a reservoir for the liquid, and made of glass. The barrel 14 has an open proximal end 14P provided with a flange 16, and a distal end 14D of generally conical shape converging away from the proximal end 14P.

The syringe 12 also has a plunger 18 mounted to be axially movable in the barrel 14 between a ready position, as shown in FIG. 1, and a position at the end of injecting liquid, as shown in FIG. 2.

The plunger 18, e.g. made of plastics material, has a proximal end 18P outside the barrel 14, and a distal end 18D inside the barrel 14 and carrying a conventional piston 20. The proximal end 18P of the plunger forms an end for driving the plunger.

The syringe 12 also has a fastener endpiece 22 having a plug 24 for closing the syringe, as shown in FIG. 1, or a needle carrier 26 as shown in FIG. 2.

The fastener endpiece 22 is generally annular in shape having a proximal end engaged in known manner on a complementary surface of the distal end 14D of the barrel 14. The fastener endpiece 22 also has a distal end for co-operating by screw-fastening with the closure plug 24 or with the needle carrier 26.

The needle carrier 26 carries a needle 28 suitable for being protected by a removable cap engaged on the needle carrier 26.

An axial channel 32 formed in the distal end 14D of the syringe barrel 14 allows liquid to pass between the barrel 14 and the needle carrier 26.

The assembly 10 also includes a safety device 33.

The device 33 comprises a first member of generally tubular shape referred to as a protective sheath 34, and a second member of generally tubular shape referred to as a syringe support 36. The support 36 is housed in the sheath 34, substantially coaxially therewith.

By way of example, the sheath 34 and the support 36 are made of plastics material.

The sheath 34 and the support 36 are movable axially relative to each other between a "needle disengagement" first position, as shown in FIG. 1, and a "needle retracted" second position as shown in FIG. 2.

The syringe barrel 14 is housed in conventional manner in the support 36. More particularly, the syringe barrel 14 is prevented from moving axially in the syringe support 36 by snap-fastening the flange 16 between a bearing seat 38 formed in the support 36 and a plurality of retractable locking abutments 40 secured to the support 36.

The safety device 33 includes retaining means for retaining the support 36 in the needle-disengaged position relative to the sheath 34. These retaining means oppose the resilient force of the return means comprising a thrust spring 42. As shown in FIG. 2, it can be seen that in the needle-disengagement position, the spring 42 is received in a groove 84 of generally annular shape, arranged in this example in the proximal end of the sheath 34. The groove 84 also serves to position the spring 42 both axially and radially.

As can be seen in FIG. 3, the retaining means comprise at least one pair of complementary retaining abutments. A first retaining abutment 44 is formed by the free end of an axial tongue 45 arranged in a proximal end of the sheath 34. This tongue 45 is elastically deformable in a radial direction. The second retaining abutment 46 is formed on a proximal end of the syringe support 36. The safety device 33 preferably has two pairs of retaining abutments 44 and 46, which pairs are diametrically opposed.

As can be seen in FIG. 1, the assembly also comprises a pad 50 interposed between the flange 16 of the syringe barrel and the bearing seat 38 of the syringe support. These elements are described in greater detail below.

Furthermore, with the exception of aspects associated with the invention that are described in greater detail below, the operation of the safety device 33 is conventional, e.g. as described in FR-A-2 830 765.

By way of example, the safety device 33 also has means for locking the sheath 34 when the needle 28 is in the retracted position. The sheath 34 also carries external grip means (not shown in the figures) for receiving the fingers of a user in order to inject the liquid by axially moving the drive end 18P of the plunger towards the grip means.

With reference to FIG. 3, there follows a description of the proximal end of the FIG. 1 syringe assembly.

The pad is made of an elastomer material and is placed in compression between the seat 38 of the syringe support and the flange 16 of the barrel. Because of the material from which it is made, its coefficients of friction with the flange and with the support, respectively, are sufficient to generate an opposing torque that prevents the syringe from turning inside the safety device, and in particular that is greater than the coefficient between the flange and the support. Such a pad serves to generate an opposing torque that prevents the syringe barrel from turning, even if a user unscrews the plug 24 or screws a needle carrier 26 into the endpiece 22.

The pad 50 presents a body in the form of an annular ring. The pad 50 also includes a plurality of lugs 52 arranged on the body, as can also be seen in FIG. 4. These lugs are arranged on a face of the body that is to come into contact with the flange 16 of the barrel 14 and also on a face of the body that is to come into contact with the seat 38. These lugs are hemispherical and they are distributed regularly over the ring 50. They serve to increase friction between the pad and the flange without the thickness of the body being excessive and thus giving rise to stresses that are too great on the abutments 40.

Figure 4:
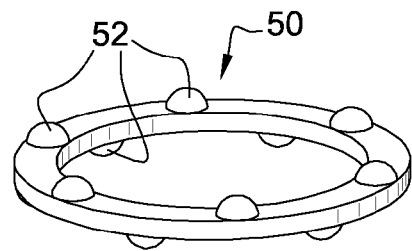
FIG. 4 is a view of a pad of the assembly of FIGS. 1 to 3.

The lugs 52 of the face that is to be in contact with the seat 38 are interposed between the lugs of the face that is to come into contact with the flange, as can be seen in FIG. 4.

The pad is generally pre-mounted on the device 33 by being wedged between the seat 38 and the abutments 40 of the syringe support, before the syringe is mounted in conventional manner on the device 33.

Several variants of the assembly shown in FIGS. 1 to 4 are outlined below.

In the following figures, the assembly is identical to that of FIGS. 1 to 4, apart from a few constructional details that are described below. References identical to those of the above figures (in particular concerning FIG. 5) designate elements that are identical.

Figure 5A:
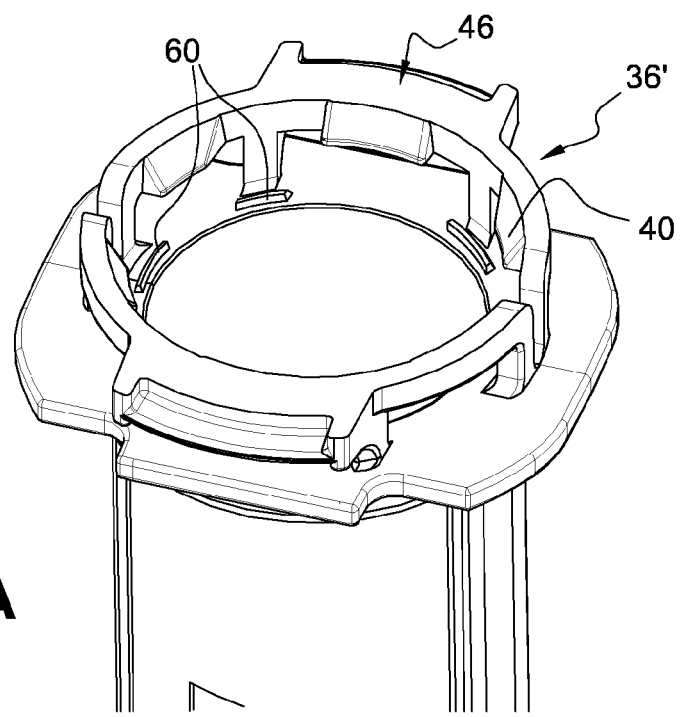
FIG. 5A is a perspective view of the proximal end of the syringe support of an assembly in another embodiment of the invention.

In FIG. 5A, the syringe support 36' has teeth 60 formed on the bearing seat 38. These teeth 60 are distributed regularly over the syringe support, and they are placed in a support zone that is distinct from the zone situated facing the abutment 40. They extend in a preferred direction corresponding to a transverse direction of the support.

Figure 5B:
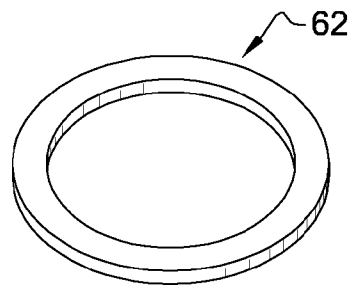
FIG. 5B is a view of a pad suitable for mounting on the syringe support of FIG. 5A.

The assembly then has a pad 62 forming a simple annular ring, as shown in FIG. 5B, without any lugs, which is easier to fabricate. The pad may then have the same thickness as the body of the pad in the above-described embodiment. In spite of the absence of lugs on the pad, proper operation of the device is nevertheless ensured. The teeth serve to increase the compression of the ring and to increase the opposing torque generated between the barrel 14 and the syringe support 36'.

Figure 6:
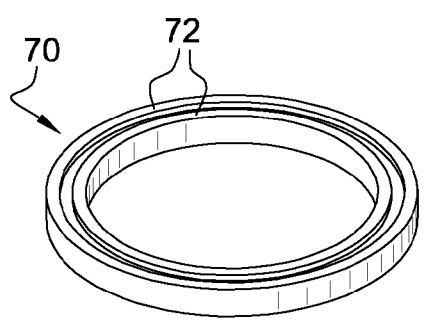
FIGS. 6 and 7 show pads of an assembly constituting a variant of that of FIG. 1.

In FIG. 6, the pad 70 comprises a body in the form of an annular ring and two peripheral ribs 72 extend all around the pad 70 from each of its radial ends. The ribs 72 project from a face of the pad that is to come into contact with the flange 16 of the syringe barrel 14.

Figure 7:
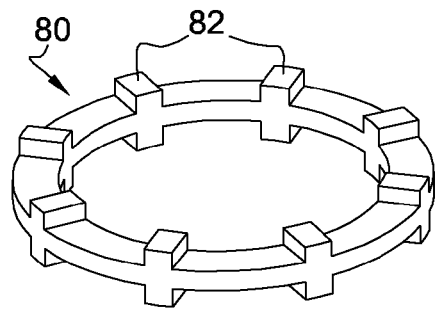

In FIG. 7, the pad 80 also comprises a body in the form of an annular ring and projections 82 projecting from the body relative to the two contact faces of the ring, respectively with the syringe barrel 14 and with the support 36. These projections are in the form of rectangular blocks and they extend over the entire radial dimension of the ring. They are distributed regularly all around the ring.

Figure 8:
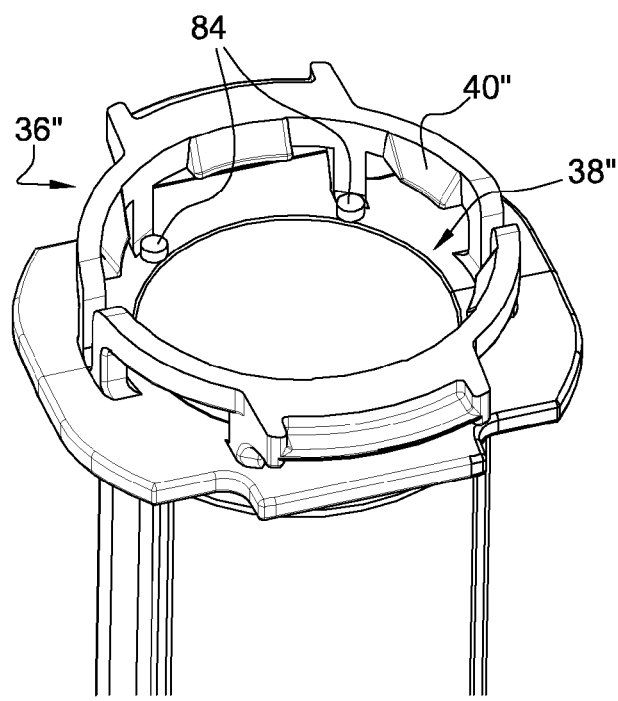
FIG. 8 is a perspective view of the proximal end of the syringe support of an assembly in a third embodiment of the invention.

In FIG. 8, the syringe support 36" has a plurality of pads 84 arranged on the seat 38" of the syringe support 36". These pads are cylindrical in shape and each of them is fitted onto the support via one of its bases. They are of a diameter that is less than the width of the seat 38. They are situated in zones of the seat that do not face any abutments 40". In this embodiment, the pads 84 are overmolded on the seat 38". They could equally well be assembled thereon.

It should be observed that the assembly of the invention is not limited to the above description. For example, the materials of the syringe barrel, of the safety devices, or of the pads could be different from those described.

The shape of the safety device may also vary from that described above. For example, the abutments 40 and 44, 46 may be shaped differently or may be distributed differently from the above description.

The assembly may also have a plurality of pads of smaller dimensions or of shapes different from those described.

The pad may also form an annular ring having projections other than those described or projections that are not regularly distributed. The projections may also be placed solely on the face of the pad that is to come into contact with the syringe support.

The pad may also be fastened, e.g. by adhesive, heat-sealing, or overmolding, to the safety device or to the syringe. It may also be engaged on the syringe before it is mounted on the safety device.

When the pads and/or the projections are integral with the safety device, they may be placed facing an abutment serving to prevent the syringe barrel from moving axially. The projections or the pad may equally well not be distributed regularly on the body of the pad and/or the seat.

The invention claimed is:

1. A syringe assembly comprising a liquid-injection syringe and a safety device, the syringe assembly comprising a syringe barrel of generally tubular shape forming a reservoir for the liquid, the safety device comprising a syringe-support member in which the syringe barrel is arranged so that the syringe support and the syringe barrel are secured together axially, the syringe barrel having a flange at a proximal end, which flange is prevented from moving in translation between firstly a peripheral bearing seat, and secondly at least one abutment of the syringe support, the assembly also includes, interposed between the seat of the support and the flange of the syringe barrel, at least one pad compressed between the seat and the flange, the pad being made of an elastic material,
   wherein at least one of the pad and the seat of the support includes at least one projection,
   wherein the pad includes a plurality of projections distributed regularly on at least one of a top or bottom face in contact with flange and/or with the seat.

2. The syringe assembly according to claim 1, wherein the at least one projection is formed on the seat and is situated in a zone distinct from a zone facing the abutment.

3. The syringe assembly according to claim 2, wherein each of the plurality of projections of the pad is constituted by an element from the following list:
   a lug of hemispherical or rectangular block shape;
   a rib extending over at least a portion of the periphery of the pad; and
   a radial rib.

4. The syringe assembly according to claim 1, wherein the pad presents a coefficient of friction with at least one of the materials of the flange or of the seat that is greater than the coefficient of friction relative to at least one of the materials of the flange and the seat relative to each other.

5. The syringe assembly according to claim 1, wherein the pad is formed by an annular ring.

6. The syringe assembly according to claim 1, wherein the syringe barrel is made of glass or of plastics material and the syringe support is made of plastics material, the plastics material of the support and/or of the barrel being in particular based on polyethylene (PE), polypropylene (PP), polycarbonate (PC), polystyrene (PS), polyester (PET, PEN), styrenic polymers (SAN), acrylic polymers (PMMA), copolymers (MBS, SMMA terpolymers), polyvinyl chloride (PVC), copolyester (PETG, PCTG, PCTA), acrylonitrile-butadiene-styrene (ABS), cyclic polyolefins such as cyclo olefin polymer (COP) and cyclic olefin copolymers (COC), polyamide (PA), SB copolymer, styrene-ethylene-butylene-styrene (SEBS), polyether block amide (PEBA), poly(lactic-co-glycolic acid)(PLGA), polyactic acid (PLA), polyhydroxyalcanoates (PHA), polyhydroxybutyrate (PHB), cellulose propionate, cellulose acetate, and any mixture of these polymers and/or copolymers.

7. The syringe assembly according to claim 1, wherein the pad is made of a thermoplastic or thermosetting elastomer material such as liquid silicone rubber (LSR), optionally halogenated butyl rubber, nitrile rubber, thermoplastic ethylene-propylene-diene monomer (EPDM), a mixture of polypropylene and of cross-linked ethylene-propylene-diene monomer (PP/EPDM), thermoplastic polyurethane (TPU), and cross-linked polyurethane (PU), styrene thermoplastics, any mixture of these polymers and/or copolymers.

8. The syringe assembly according to claim 1, wherein the liquid-injection syringe is a luer lock syringe.

9. The syringe assembly according to claim 1, wherein the liquid-injection syringe is a luer lock syringe.

10. The syringe assembly according to claim 1, wherein the projections are hemispherical lugs.

11. The syringe assembly according to claim 1, wherein the projections have a substantially rectangular shape.

* * * * *